United States Patent
Niederberger

(10) Patent No.: US 9,729,977 B2
(45) Date of Patent: Aug. 8, 2017

(54) METHOD FOR OPERATING A HEARING DEVICE CAPABLE OF ACTIVE OCCLUSION CONTROL AND A HEARING DEVICE WITH USER ADJUSTABLE ACTIVE OCCLUSION CONTROL

(71) Applicant: Sonova AG, Stafa (CH)

(72) Inventor: Andre Niederberger, Mannedorf (CH)

(73) Assignee: SONOVA AG, Staefa (CH)

( * ) Notice: Subject to any disclaimer, the term of this patent is extended or adjusted under 35 U.S.C. 154(b) by 0 days.

(21) Appl. No.: 14/896,482

(22) PCT Filed: Jun. 12, 2013

(86) PCT No.: PCT/EP2013/062075
§ 371 (c)(1),
(2) Date: Dec. 7, 2015

(87) PCT Pub. No.: WO2014/198306
PCT Pub. Date: Dec. 18, 2014

(65) Prior Publication Data
US 2016/0150330 A1    May 26, 2016

(51) Int. Cl.
*H04R 25/00* (2006.01)
*A61F 2/08* (2006.01)
(Continued)

(52) U.S. Cl.
CPC ............. *H04R 25/505* (2013.01); *A61F 2/08* (2013.01); *G06F 3/167* (2013.01);
(Continued)

(58) Field of Classification Search
CPC ... H04R 2460/05; H04R 25/50; H04R 25/505
See application file for complete search history.

(56) References Cited

U.S. PATENT DOCUMENTS 8,208,650 B2    6/2012 Joho
2008/0063228 A1    3/2008 Meijia
(Continued)

FOREIGN PATENT DOCUMENTS

DE    10 2009 018 811 A1    6/2010
EP          2 640 095 A1    9/2013
(Continued)

OTHER PUBLICATIONS

International Search Report for PCT/EP2013/062075 dated Aug. 11, 2015.
Written Opinion for PCT/EP2013/062075 dated Aug. 11, 2015.

*Primary Examiner* — Matthew Eason
(74) *Attorney, Agent, or Firm* — Pearne & Gordon LLP

(57) ABSTRACT

A method for operating a hearing device for being worn at least partially within an ear canal of a user, including an ear canal microphone, a filtering unit and an electrical-to-acoustical converter, capable of active occlusion control (AOC) and allowing the user to adjust the AOC functionality according to his or her preferences. The method includes picking up an ear canal internal sound at the microphone which provides a signal representative of the internal sound, filtering the signal with the filtering unit to reduce a perceived level of body sounds produced by the user, providing the filtered signal to the converter which outputs sound into the ear canal, and changing at least one setting or parameter of the filtering unit in dependence of a control signal, wherein the control signal is initiated by the user. Moreover, a hearing device adapted to perform the method is provided.

24 Claims, 2 Drawing Sheets

(51) Int. Cl.
*G10K 11/178* (2006.01)
*G06F 3/16* (2006.01)
*A61F 11/14* (2006.01)

(52) U.S. Cl.
CPC ......... *G10K 11/1788* (2013.01); *H04R 25/30* (2013.01); *H04R 25/50* (2013.01); *H04R 25/558* (2013.01); *A61F 2011/145* (2013.01); *G10K 2210/1081* (2013.01); *H04R 25/70* (2013.01); *H04R 2225/023* (2013.01); *H04R 2225/025* (2013.01); *H04R 2225/61* (2013.01); *H04R 2460/05* (2013.01)

(56) References Cited

U.S. PATENT DOCUMENTS

| 2008/0107287 | A1 | 5/2008 | Beard |
| 2009/0034765 | A1 | 2/2009 | Boillot |
| 2010/0220881 | A1 | 9/2010 | Arndt |

FOREIGN PATENT DOCUMENTS

| EP | 2 104 376 B1 | 11/2014 |
| WO | 2008/083315 A2 | 7/2008 |
| WO | 2008/131342 A1 | 10/2008 |
| WO | 2012/085514 A2 | 6/2012 |

METHOD FOR OPERATING A HEARING DEVICE CAPABLE OF ACTIVE OCCLUSION CONTROL AND A HEARING DEVICE WITH USER ADJUSTABLE ACTIVE OCCLUSION CONTROL

TECHNICAL FIELD

The present invention is related to a method of operating a hearing device capable of active occlusion control (AOC) as well as to a hearing device adapted to perform the method. In particular, the present invention is directed to allowing the user of the hearing device to adjust an active occlusion control functionality of a hearing device according to his or her preferences.

BACKGROUND OF THE INVENTION

Within the context of the present invention hearing devices for instance comprise hearing aids, such as behind-the-ear (BTE), in-the-ear (ITE) or completely-in-canal (CIC) hearing aids, earphones, hearing protection devices, as well as ear-level communication, noise reduction and sound enhancement devices. Hearing aids (also commonly referred to as hearing instruments or hearing prostheses) are specifically utilised by persons having a hearing impairment, in order to compensate their hearing loss and improve their hearing ability as much as possible to the level of a person with normal hearing.

A frequent complaint of users of hearing devices, especially when they start wearing them for the first time, is that the sound of their own voice is too loud or that it sounds like they are talking into a barrel. This so-called "occlusion effect" occurs when an object fills the outer portion of a person's ear canal (commonly also referred to as the auditory canal) and is especially pronounced when the ear canal is sealed, e.g. by an otoplastic. It is caused by bone-conducted sound vibrations reverberating off the object filling the ear canal. The occlusion effect can be reduced by employing large vents. However, large vents give rise to increased acoustic feedback, so the amount of amplification that is applied by a hearing device must be limited in order to avoid it generating unpleasant whistling and squealing sounds. Alternatively, methods exist for actively reducing occlusion such as described in EP 2 104 376 A2. Hereby, sound in the auditory canal is picked up by a microphone and the microphone signal is applied to a filter. The filtered microphone signal is fed back to an input of a receiver which is used to emit the sound into the auditory canal. At least part of a transducer transmission function, which is defined for the transmission path from the input of the receiver via the auditory canal to the output of the microphone, is measured and the filter can for instance be adjusted as a function thereof. Typically, a filter which is assumed to have optimal characteristics is selected during the process of hearing device fitting, i.e. adjusting the hearing device settings to the needs of the user, by a hearing device professional such as a hearing device acoustician based on a variety of criteria. A very important criterion is the user's subjective perception of his/her own voice. However, the user generally requires time to get used to a new hearing device and therefore the settings must be fine-tuned after a certain time period of using the hearing device especially in real life listening situations. Therefore, frequently the user will have to return to the hearing device professional multiple times in order to readjust and improve the settings of the hearing device.

SUMMARY OF THE INVENTION

It is an object of the present invention to improve the process of adjusting a hearing device capable of active occlusion control (AOC) to the preferences of its user.

The object of the invention is achieved by the method according to claim 1 and by the hearing device according to claim 14. Specific embodiments are provided in the dependent claims.

The present invention is first directed to a method for operating a hearing device adapted for being worn at least partially within an ear canal of a user, the hearing device comprising an ear canal microphone, a filtering unit and an electrical-to-acoustical converter, the method comprising the steps of:
  picking up an ear canal internal sound at an input of the ear canal microphone which outputs an ear canal signal representative of the ear canal internal sound;
  filtering the ear canal signal with the filtering unit configured to reduce a perceived level of body sounds produced by the user, the filtering unit outputting a filtered ear canal signal;
  providing the filtered ear canal signal to an input of the electrical-to-acoustical converter which outputs sound into the ear canal;
  changing at least one setting or parameter of the filtering unit in dependence of a control signal,
wherein the control signal is initiated by the user.

This allows the user of the hearing device to try out other settings for AOC after having experienced the sound of the own voice and other body sounds for some time to see if the perception of the own voice can be further improved. In this way the user can take control of the AOC functionality and alter his/her perception of the sound of the own voice, for instance depending on the listening situation or mood the user is presently in. This has the advantage that the user does not have to return to the fitter's office and repeat the necessary fitting steps, which is more time-consuming and a very costly process.

In an embodiment of the proposed method the control signal is initiated by the user by at least one of the following actions:
  operating a control element such as for instance a switch, a push button, a slider, a dial, a wheel, a touch sensitive element, such as for example a touch screen;
  activating or powering on the hearing device;
  issuing a voice command;
  sending the control signal from a remote unit, such as for instance a remote control unit, a mobile device such as for example a smart phone, or a computer, to the hearing device.

In this way the user can alter the impression of the intensity of the occlusion cancelling system and try out various settings until finding those with which he/she feels most comfortable with.

In a further embodiment of the method the filtering unit has a user-adjustable transfer function, and wherein the at least one setting or parameter of the filtering unit for which a change is caused is at least one of the following:
  a gain;
  a centre frequency;
  an attenuation at the centre frequency;
  the transfer function;

a set of filtering coefficients, in particular a set selected from a plurality of predetermined sets of filtering coefficients.

In a further embodiment of the method the filtering unit comprises a plurality of bi-quads, in particular up to 5 (yielding a filter order of 10), wherein the at least one setting or parameter of the filtering unit for which a change is caused is a number of active bi-quads, in particular the number being controllable in the range from 3 to 5. Therewith, the filter order can be varied dependent on the control signal.

This provides the user with a variety of parameters to change and permits the user to precisely adjust the way in which he/she prefers to perceive his/her own voice. The user can for instance also select between various, predetermined filter settings or different sets of optimal filter parameters determined during fitting at the fitter's office. The different sets of optimal filter parameters can for instance be stored in a non-volatile memory (NVM) of the hearing device.

In a further embodiment the method further comprises limiting the change of the at least one setting or parameter of the filtering unit to a predetermined range or a range determined dependent on a status of the hearing device, so that safe operation of the hearing device is assured for the user. In this way, for instance the gain is kept within certain safe limits, so that dangerously loud sound levels or unstable operation of the hearing device are avoided.

In a further embodiment of the method the change of the at least one setting or parameter of the filtering unit is dependent on data provided from a location remote from the hearing device. In this way alternative settings proposed by the fitter can be downloaded by the user or the fitter can provide direct remote support and change settings of the AOC system without the user having to go to the fitter's office.

In a further embodiment of the method the hearing device further comprises an ambient microphone and a signal processing unit, and the method further comprises the steps of:
  picking up ambient sound at an input of the ambient microphone which provides an audio signal representing the ambient sound;
  processing the audio signal in the signal processing unit according to a hearing program selected, either manually by the user or automatically by the hearing device, from a plurality of hearing programs, and providing a processed audio signal;
  combining the processed audio signal and the filtered ear canal signal,
wherein the change of the at least one setting or parameter of the filtering unit is dependent on the selected hearing program. In this way it is possible to assist the user in adjusting the AOC by for instance limiting the setting, e.g. the parameters and/or the range of the values that can be assigned to these parameters, based on the hearing program (e.g. speech, speech in noise, etc.) the hearing device is presently employing.

In a further embodiment the method further comprises determining an acoustic situation by the hearing device, and wherein the change of the at least one setting or parameter of the filtering unit is dependent on the determined acoustic situation. In this way it is possible to assist the user in adjusting the AOC by for instance limiting the setting, e.g. the parameters and/or the range of the values that can be assigned to these parameters, based on the hearing or listening situation the user is presently in.

In a further embodiment of the method the change of at least one setting or parameter of the filtering unit is dependent on the number of times the control signal has been initiated, in particular on the number of times the hearing device has been activated or powered on. In this way it is for instance possible to limit the way in which the user makes changes to the AOC system e.g. at the beginning when starting to use a new hearing device, in order to prevent premature changes by the user, when insufficient time has passed to actually get used to certain hearing device settings. On the other hand it for instance allows the fitter to provide a set of predetermined settings where every time when the hearing device is turned on a new set of settings is applied.

In a further embodiment of the method the at least one setting or parameter of the filtering unit is changed over time from a start value to an end value, particularly the change is incrementally applied. In this way a slight change of the settings can be made for instance each time the hearing device is turned on or every time the user initiates the control signal.

In a further embodiment of the method a speed at which and/or an increment/decrement by which the at least one setting or parameter of the filtering unit is changed is adjustable. In this way it is possible to influence the speed with which for instance the end value is reached. The rate of change can for example be set by the fitter during the fitting process, and can for instance be changed from a remote location as part of a remote support process.

In a further embodiment of the method the change of the at least one setting or parameter of the filtering unit is dependent on a timer signal. This allows to change the settings for instance according to a predefined function of time.

In a further embodiment the method further comprises detecting whether a body sound of the user is present or not, and wherein the change of the at least one setting or parameter of the filtering unit is only carried out if a body sound of the user is detected as being present upon the control signal being initiated by the user, in particular if a body sound of the user is detected as being present within less than 10 s after the control signal has been initiated. In this way for instance changes are effected only if the user initiates a control signal and also speaks or makes another body sound. This makes it possible to reuse a control element which is assigned to perform another function for controlling the AOC settings when manipulated in conjunction with the presence of the user's own voice. Furthermore, the control element could be used to initiate acceptance of voice command issued by the user.

In a further embodiment of the method the changed at least one setting or parameter of the filtering unit is stored in a storage unit of the hearing device. The storage unit can for instance comprise non-volatile memory (NVM). In this way a change made be the user can be made permanently available, for instance after turning on and off the hearing device, or it can at least be made available for later use, e.g. when the user is in the same or a similar listening situation or the hearing device is employing the same hearing program.

Moreover, the present invention is directed to a hearing device adapted for being worn at least partially within an ear canal of a user, the hearing device comprising:
  an ear canal microphone;
  a filtering unit configurable and/or controllable to reduce a perceived level of body sounds produced by the user;
  an electrical-to-acoustical converter; and
  a control unit, wherein an output of the ear canal microphone is connected to an input of the filtering unit, an output of the filtering unit is operationally connected to an input of the electrical-to-acoustical converter, and an output of the control unit is connected to a control input of the filtering unit, and wherein the control unit is operationally connected or connectable to a control element, and the control unit is adapted to receive a control signal initiated by the user and upon receiving the control signal to cause a change of at least one setting or parameter of the filtering unit.

In an embodiment the hearing device further comprises at least one of:
- a control element, such as for instance a switch (e.g. an on/off switch), a push button, a slider, a dial, a wheel, a touch sensitive element, such as for instance a touch screen, adapted to provide the control signal upon being operated by the user;
- a voice command detection unit;
- means for receiving the control signal from a remote device, such as for instance a remote control unit, a mobile device such as for example a smart phone, or a computer, to the hearing device.

In a further embodiment of the hearing device the filtering unit has a user-adjustable transfer function, and wherein the control unit is further adapted to cause a change of at least one of the following settings or parameters of the filtering unit:
- a gain;
- a centre frequency;
- an attenuation at the centre frequency;
- the transfer function;
- a set of filtering coefficients, in particular a set selected from a plurality of predetermined sets of filtering coefficients.

In a further embodiment of the hearing device the filtering unit comprises a plurality of bi-quads, in particular up to 5 (yielding a filter order of 10), wherein the at least one setting or parameter of the filtering unit for which a change is caused by the control unit is a number of active bi-quads, in particular the number being controllable in the range from 3 to 5.

In a further embodiment of the hearing device the control unit is further adapted to limit the change of the at least one setting or parameter of the filtering unit to a predetermined range or a range determined dependent on a status of the hearing device, such as to provide safe operation of the hearing device for the user.

In a further embodiment of the hearing device the control unit is further adapted to change the at least one setting or parameter of the filtering unit dependent on data receivable from a location remote from the hearing device.

In a further embodiment the hearing device further comprises an ambient microphone and a signal processing unit, wherein an output of the ambient microphone is connected to a first input of the signal processing unit, and wherein the output of the filtering unit is connected to a second input of the signal processing unit, and wherein an output of the signal processing unit is connected to the input of the electrical-to-acoustical converter, an wherein the signal processing unit is adapted to process a signal provided at the first input according to a hearing program selected, either manually by the user or automatically by the hearing device, from a plurality of hearing programs to yield a processed signal, and to combine the processed signal with a signal provided at the second input to yield a combined signal at the output of the signal processing unit, and wherein the control unit is further adapted to change the at least one setting or parameter of the filtering unit dependent on the selected hearing program.

In a further embodiment the hearing device further comprising a classification unit adapted to determine an acoustic situation, wherein the control unit is further adapted to change the at least one setting or parameter of the filtering unit dependent on the determined acoustic situation.

In a further embodiment the hearing device further comprising a counter adapted to count the number of times the control signal has been initiated, wherein the control unit is further adapted to change the at least one setting or parameter of the filtering unit dependent on the number of times the control signal has been initiated, in particular on the number of times the hearing device has been activated or powered on.

In a further embodiment of the hearing device the control unit is further adapted to incrementally change the at least one setting or parameter of the filtering unit over time from a start value to an end value.

In a further embodiment of the hearing device a speed at which and/or an increment/decrement by which the at least one setting or parameter of the filtering unit is changed is adjustable.

In a further embodiment the hearing device further comprises a timer, wherein the change of the at least one setting or parameter of the filtering unit is dependent on a timer signal from the timer.

In a further embodiment the hearing device further comprises an own voice detection unit for detecting whether a body sound of the user is present or not, and wherein the control unit is further adapted to only carry out the change of the at least one setting or parameter of the filtering unit if a body sound of the user is detected as being present upon the control signal being initiated by the user, in particular if a body sound of the user is detected as being present within less than 10 s after the control signal has been initiated.

In a further embodiment the hearing device further comprises a storage unit for storing the changed at least one setting or parameter of the filtering unit.

It is to be pointed out that combinations of the above-mentioned embodiments give rise to even further, more specific embodiments according to the present invention.

BRIEF DESCRIPTION OF THE DRAWINGS

The present invention is further explained below by means of non-limiting specific embodiments and with reference to the accompanying drawings. What is shown in the figures is the following.

In the figures, like reference signs refer to like parts.

DETAILED DESCRIPTION OF THE INVENTION

Figure 1:
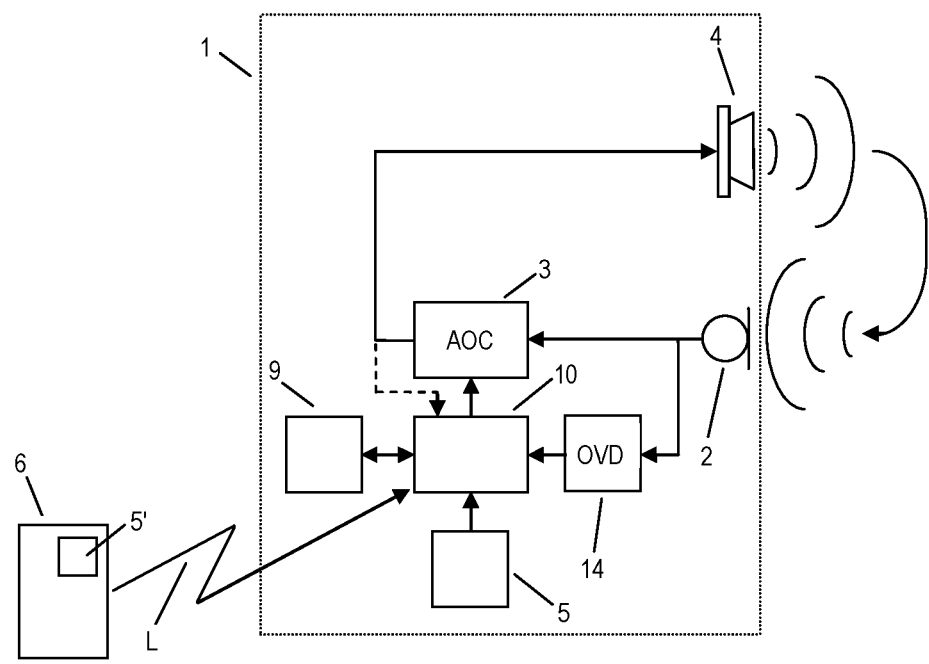
FIG. 1 a schematic high-level block diagram of an exemplary hearing device according to the present invention.
Figure 4:
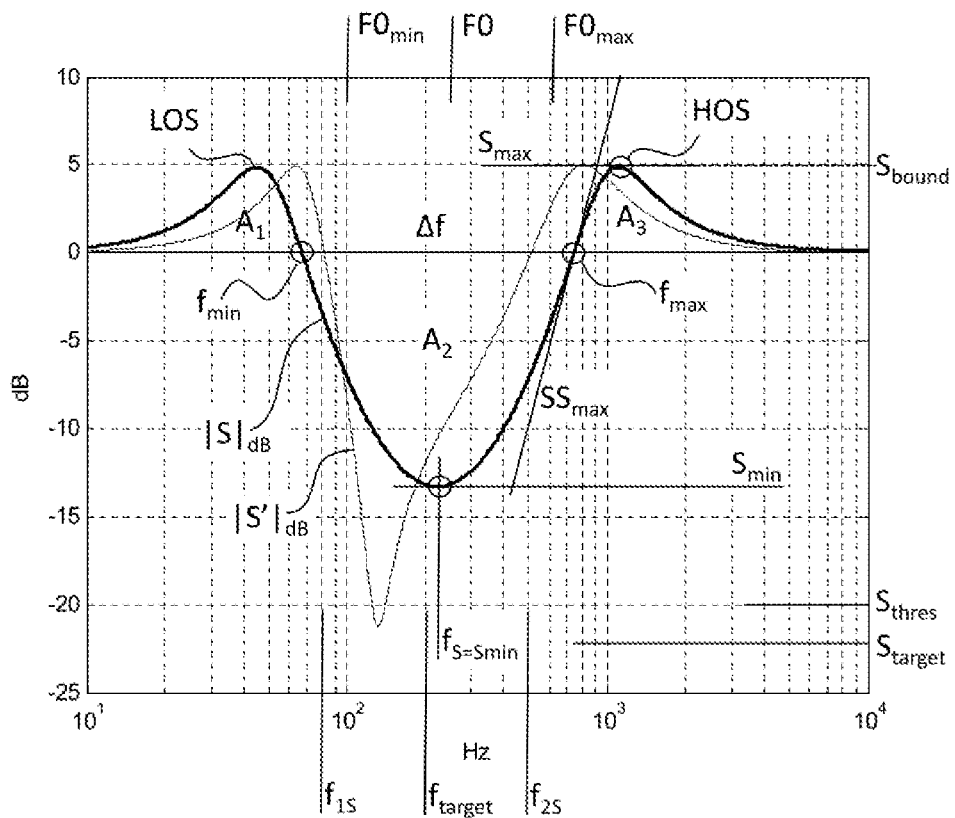
FIG. 4 a graph of an exemplary sensitivity curve for a hearing device employing an AOC scheme having a minimum sensitivity at 230 Hz.

In FIG. 1 a high-level block diagram of an exemplary hearing device 1 according to the present invention is schematically depicted. The sound emitted by the receiver 4 into the ear canal of the user of the hearing device 1 is picked-up by an ear canal microphone 2, for instance located at the proximal end of the hearing device 1 and directed towards the eardrum in order to be able to sense sounds present within the ear canal, especially those present between the proximal end of the hearing device 1 and the ear drum. The signal provided by the ear canal microphone 2 which represents the sound within the ear canal is filtered by a filtering unit 3, whose transfer function is adapted to generate a signal at its output, which when emitted into the ear canal reduces the level of body sounds, such as the user's own voice, swallowing and chewing sounds, present in the sound within the ear canal. The filtered signal at the output of the filtering unit 3 is then provided to the receiver 4, which emits it into the ear canal, where the sound signal produced by the receiver 4 is combined with body sounds, e.g. the "own voice" of the user. The settings of the filtering unit 3, e.g. filter parameters, initially determined during a fitting process by a hearing device professional such as an audiologist or acoustician, during which the hearing device is individually adjusted to the specific needs and preferences of the user of the hearing device. Thereby the transfer function of the filtering unit 3 is adjusted such that when the user hears his/her own voice that it sounds as natural and familiar as possible to the user, and the occlusion effect is minimised, i.e. hollow, booming low-frequency sound is largely cancelled in the sound present within the ear canal. Since the user only gradually gets used to the hearing device, the fitting needs to be adjusted or fine-tuned once or more after the initial fitting process. In order to avoid having to visit the fitter's office to improve the settings of the filtering unit 3, the hearing device comprises a control element 5, which can be manually operated by the user and such that the user can initiate a control signal. Furthermore, the filtering unit 3 has a user-adjustable transfer function, for instance with a notch, the centre frequency and attenuation of which are adjustable, e.g. within the range from 100 Hz to 300 Hz, and 10 dB to 30 dB, respectively. The control element 5 is either integrated into the hearing device 1 or located remotely from the hearing device 1, e.g. on a remote unit 6 such as a wireless remote control device with a built-in control element 5'. The control element 5, 5' can for instance take on the form of a switch, a push button, a slider, a dial, a wheel or a touch sensitive element. The remote device by for instance be a mobile telephone, e.g. a smartphone, a tablet computer, a laptop or a desktop computer, etc. for example comprising a touch pad or a touch screen providing a control element 5'. The remote device 6 is operationally connected with the hearing device 1, more specifically with a control unit 10 within the hearing device 1, whereby the link between the remote device 6 and the hearing device 1 is preferably established via a wireless connection, but alternatively may also be provided via a special cable, such as a programming cable that can be plugged into a special socket provided at the hearing device 1. The control signal can for instance alternatively also be initiated when activating or powering on the hearing device 1 or by a voice command issued by the user (e.g. pick-up either by the ear canal microphone 2 or alternatively by the ambient microphone 7 shown in FIG. 2). The control signal initiated by the user is applied to the control unit 10, where depending on the type of inputs means provided as the control element, the control signal is decoded or mapped onto a specific setting or parameter of the filtering unit 3. For instance also multiple settings or parameters of the filtering unit 3 can be changed at once dependent on a certain control signal. For example multiple sets of predetermined filter coefficients can be stored within the storage unit 9 of the hearing device 1. When the control unit 1 receives a certain control signal it retrieves a particular one of the multiple sets of filter coefficients and provides the selected set to the filtering unit 3 in order to change its transfer function accordingly. The user can for instance vary the transfer function of the filtering unit 3 such that the sensitivity curve shown in FIG. 4 is achieved, which provides maximal occlusion reduction at around 230 Hz. The sensitivity S is defined as $S(f)=1/(1+P(f) \cdot C(f))$, where $P(f)$ is the transfer function from the output of the receiver 2 to the input of the ear canal microphone 4, and $C(f)$ is the transfer function of the filtering unit 3. By changing the transfer function $C(f)$ of the filtering unit 3, the user can shift the frequency $f_{Smin}$ exhibiting minimal sensitivity $S_{min}$, e.g. within the range from 100 to 300 Hz, and thus adapt his or her perception of the own voice according to personal preferences. A further possible function of the control unit 10 is to ensure that any changes of the setting(s) or parameter(s) of the filtering unit 3 remain within certain predetermined limits, such that safe operation of hearing device 1 is maintained for the user (e.g. keeping the output sound pressure level below a maximum value). This can for instance also be achieved by the control unit 10 monitoring the signal applied to the receiver 4 (or the signal at the output of the filtering unit 3; cf. dashed line in FIG. 1). Data affecting the change of the setting(s) or parameter(s) of the filtering unit 3 may also be provided from the remote device 6. E.g. new sets of filter coefficients can be downloaded by the hearing device 1 from the remote device 6 via the link L.

Figure 2:
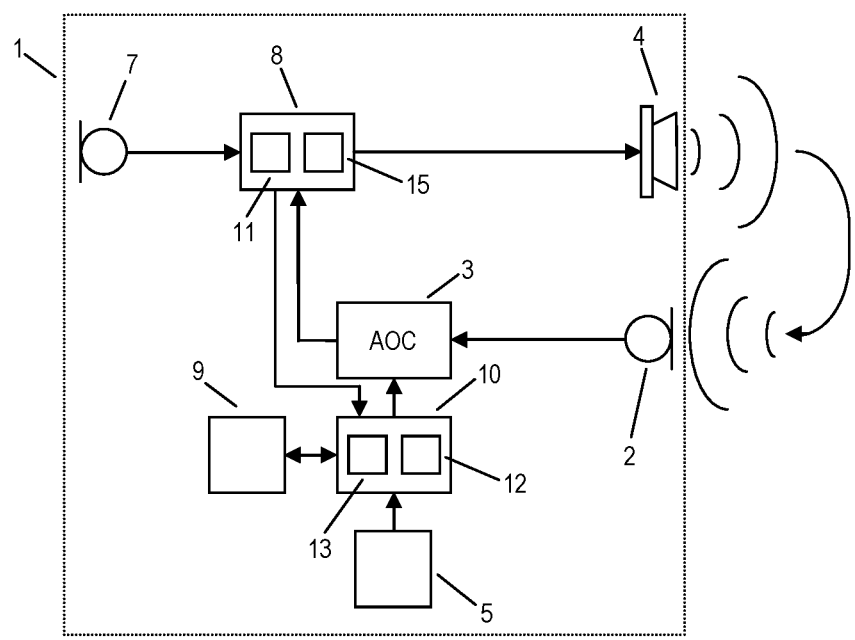
FIG. 2 a schematic block diagram of a further exemplary hearing device according to the present invention.
Figure 3:
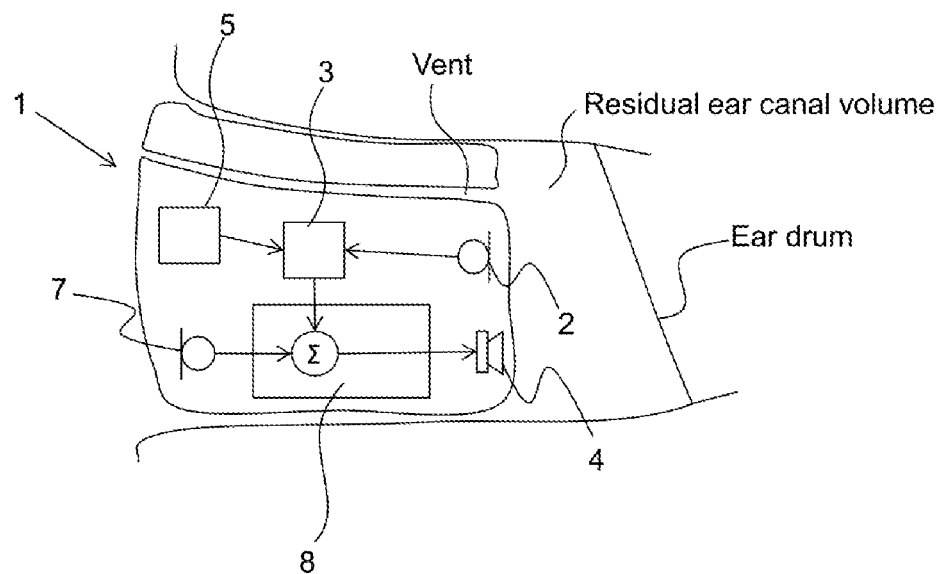
FIG. 3 a schematic block diagram of a further exemplary hearing device according to the present invention inserted in an ear canal.

An alternative exemplary embodiment of a hearing device 1 according to the present invention is schematically depicted in FIG. 2 as well as in FIG. 3, where the hearing device 1 is shown inserted in the ear canal. Here the hearing device 1 further comprises a signal processing unit which amongst other things combines the signal provided by the filtering unit 3 with a possibly processed version of a signal provided by an ambient microphone 7. The ambient microphone 7 is located at the distal end of the hearing device 1 (i.e. directed towards the outside of the ear canal) and picks up sound from the ambient surroundings of the user, i.e. from outside the ear canal. The (processed version of the) signal from the ambient microphone 7 is applied to a pre-equalisation unit 15 comprised in the signal processing unit 8, before it is combined with the signal provided by the filtering unit 3. Pre-equalisation boosts the (processed) signal from the ambient microphone 7 at those frequencies, where the AOC loop will subsequently attenuate signal components at these frequencies. The pre-equalisation unit 15 thus ensures that the (processed) signal from the ambient microphone 7 remains essentially unaffected by the AOC. The signal from the ambient microphone is typically processed according to a signal processing scheme using certain signal processing settings suitable for the current listening situation. This is commonly achieved by determining the current listening situation with the help of a sound classification unit 11 and then automatically selecting by the hearing device 1 a hearing program associated with the determined current acoustic/listening situation. In such a hearing device 1 the application of a change requested by the user by initiating the control signal can be made dependent upon the current acoustic situation determined by the sound classification unit 11. Moreover, the requested change can be stored in the storage unit 9 and be associated with the hearing program in use when the change was initiated, such that when the hearing program is selected in the future also the associated setting(s) or parameter(s) of the filtering unit 3 are then also selected. Changes of the setting(s) or parameter(s) of the filtering unit 3 may also be made in dependence of the number of times the control signal has been initiated, in particular on the number of times the hearing device has been activated or powered on. For this purpose a counter 12 is provided in the control unit 10 to keep track of the number of times the control signal has been initiated or the hearing device has been activated and changes have been applied to the setting(s) or parameter(s) of the filtering unit 3. For example, each time the counter 12 is incremented setting(s) or parameter(s) of the filtering unit 3 are also incrementally changed beginning from a start value until an end value has been reached at which point no further changes take effect. Such incremental changes can also be triggered automatically dependent on a timer signal provided by a timer 13 also located in the control unit 10. The rate of change of such a time-based or counter-based update scheme for the setting(s) or parameter(s) of the filtering unit 3 can also be adjusted, in particular by the fitter, but optionally also by the user of the hearing device 1. Furthermore, changes of the setting(s) or parameter(s) of the filtering unit 3 may for instance only take effect if when upon the user initiating the control signal the presence of the user's own voice is detected. For this purpose an own voice detection (OVD) unit 14 is provided in the hearing device 1 (explicitly depicted in FIG. 1, but not show in FIG. 2 although also possibly as part of a hearing device as exemplified in FIG. 2). In this way it can for instance be ensured that voice commands issued by someone other than the user are taken into account by the hearing device. Furthermore, changes of the setting(s) or parameter (s) of the filtering unit 3 initiated by the user can for instance be made dependent on an assessment the user's own voice signal performed the own voice detection unit upon the user initiating a change and speaking such that the own voice sound is present in the ear canal.

What is claimed is:

1. A method for operating a hearing device (1) adapted for being worn at least partially within an ear canal of a user, the hearing device (1) comprising an ear canal microphone (2), a filtering unit (3), an electrical-to-acoustical converter (4), an ambient microphone (7), and a signal processing unit (8), the method comprising the steps of:
   picking up an ear canal internal sound at an input of the ear canal microphone (2) which outputs an ear canal signal representative of the ear canal internal sound;
   filtering the ear canal signal with the filtering unit (3) configured to reduce a perceived level of body sounds produced by the user, the filtering unit (3) providing a filtered ear canal signal;
   picking up ambient sound at an input of the ambient microphone (7) which provides an audio signal representing the ambient sound;
   processing the audio signal in the signal processing unit (8) according to a hearing program selected, either manually by the user or automatically by the hearing device (1), from a plurality of hearing programs, and providing a processed audio signal;
   combining the processed audio signal and the filtered ear canal signal to yield a combined signal;
   providing the combined signal to an input of the electrical-to-acoustical converter (4) which outputs sound into the ear canal;
   changing at least one setting or parameter of the filtering unit (3) in dependence of a control signal, wherein the change of the at least one setting or parameter of the filtering unit (3) is dependent on the selected hearing program, and
   wherein the control signal is initiated by the user.

2. The method of claim 1, wherein the control signal is initiated by the user by at least one of the following actions:
   operating a control element (5) comprising at least one of a switch, a push button, a slider, a dial, a wheel, a touch sensitive element, and a touch screen;
   activating or powering on the hearing device (1);
   issuing a voice command;
   sending the control signal from a remote unit (6), to the hearing device (1), wherein the remote unit (6) is at least one of a remote control unit, a mobile device, a smart phone, and a computer.

3. The method of claim 1, wherein the filtering unit (3) has a user-adjustable transfer function, and wherein the at least one setting or parameter of the filtering unit (3) for which a change is caused is at least one of the following:
   a gain;
   a centre frequency;
   an attenuation at the centre frequency;
   the transfer function;
   a set of filtering coefficients selected from a plurality of predetermined sets of filtering coefficients;
   a filter order corresponding to a number of active bi-quads comprised in the filtering unit (3), wherein the number is controllable in the range from 3 to 5.

4. The method of claim 1, further comprising limiting the change of the at least one setting or parameter of the filtering unit (3) to a predetermined range or a range determined dependent on a status of the hearing device (1), to provide safe operation of the hearing device (1) for the user.

5. The method of claim 1, wherein the change of the at least one setting or parameter of the filtering unit (3) is dependent on data provided from a location remote from the hearing device (1).

6. The method of claim 1, further comprising determining an acoustic situation by the hearing device (1), and wherein the change of the at least one setting or parameter of the filtering unit (3) is dependent on the determined acoustic situation.

7. The method of claim 1, wherein the change of at least one setting or parameter of the filtering unit (3) is dependent on the number of times the control signal has been initiated, corresponding to the number of times the hearing device (1) has been activated or powered on.

8. The method of claim 1, wherein the at least one setting or parameter of the filtering unit (3) is incrementally changed over time from a start value to an end value.

9. The method of claim 8, wherein a speed at which and/or an increment/decrement by which the at least one setting or parameter of the filtering unit (3) is changed is adjustable.

10. The method of claim 8, wherein the change of the at least one setting or parameter of the filtering unit (3) is dependent on a timer signal.

11. A method for operating a hearing device (1) adapted for being worn at least partially within an ear canal of a user, the hearing device (1) comprising an ear canal microphone (2), a filtering unit (3) and an electrical-to-acoustical converter (4), the method comprising the steps of:
   picking up an ear canal internal sound at an input of the ear canal microphone (2) which outputs an ear canal signal representative of the ear canal internal sound;

filtering the ear canal signal with the filtering unit (3) configured to reduce a perceived level of body sounds produced by the user, the filtering unit (3) providing a filtered ear canal signal;

providing the filtered ear canal signal to an input of the electrical-to-acoustical converter (4) which outputs sound into the ear canal;

changing at least one setting or parameter of the filtering unit (3) in dependence of a control signal, wherein the control signal is initiated by the user;

detecting whether a body sound of the user is present or not, and wherein the change of the at least one setting or parameter of the filtering unit (3) is only carried out if a body sound of the user is detected as being present upon the control signal being initiated by the user or if a body sound of the user is detected as being present within less than 10 s after the control signal has been initiated.

12. The method of claim 1, wherein the changed at least one setting or parameter of the filtering unit (3) is stored in a storage unit (9) of the hearing device (1).

13. A hearing device (1) adapted for being worn at least partially within an ear canal of a user, the hearing device (1) comprising:
   an ear canal microphone (2);
   a filtering unit (3);
   an electrical-to-acoustical converter (4);
   an ambient microphone (7);
   a signal processing unit (8), wherein an output of the ambient microphone (7) is connected to a first input of the signal processing unit (8), the output of the filtering unit (3) is connected to a second input of the signal processing unit (8), and wherein an output of the signal processing unit (8) is connected to the input of the electrical-to-acoustical converter (4);
   a control unit (10),
   wherein an output of the ear canal microphone (2) is connected to an input of the filtering unit (3), an output of the filtering unit (3) is operationally connected to an input of the electrical-to-acoustical converter (4), and an output of the control unit (10) is connected to a control input of the filtering unit (3), and wherein the control unit (10) is operationally connected or connectable to a control element (5, 5'), and the control unit (10) is adapted to receive a control signal initiated by the user and upon receiving the control signal to cause a change of at least one setting or parameter of the filtering unit (3), wherein the signal processing unit (8) is adapted to process a signal provided at the first input of the signal processing unit (8) according to a hearing program selected, either manually by the user or automatically by the hearing device (1), from a plurality of hearing programs to yield a processed signal, and to combine the processed signal with a signal provided at the second input of the signal processing unit (8) to yield a combined signal at the output of the signal processing unit (8), and wherein the control unit (10) is further adapted to change the at least one setting or parameter of the filtering unit (3) dependent on the selected hearing program.

14. The hearing device (1) of claim 13, further comprising at least one of:
   a control element (5), comprising at least one of a switch, a push button, a slider, a dial, a wheel, a touch sensitive element, and a touch screen, adapted to provide the control signal upon being operated by the user;
   a voice command detection unit;
   means for receiving the control signal from a remote device (6), to the hearing device (1), wherein the remote device (6) is at least one of a remote control unit, a mobile device a smart phone, and a computer.

15. The hearing device (1) of claim 13, wherein the filtering unit (3) has a user-adjustable transfer function, and wherein the control unit (10) is further adapted to cause a change of at least one of the following settings or parameters of the filtering unit (3):
   a gain;
   a centre frequency;
   an attenuation at the centre frequency;
   the transfer function;
   a set of filtering coefficients selected from a plurality of predetermined sets of filtering coefficients;
   a filter order corresponding to a number of active bi-quads comprised in the filtering unit (3), wherein the number is controllable in the range from 3 to 5.

16. The hearing device (1) of claim 13, wherein the control unit (10) is further adapted to limit the change of the at least one setting or parameter of the filtering unit (3) to a predetermined range or a range determined dependent on a status of the hearing device (1), to provide safe operation of the hearing device (1) for the user.

17. The hearing device (1) of claim 13, wherein the control unit (10) is further adapted to change the at least one setting or parameter of the filtering unit (3) dependent on data receivable from a location remote from the hearing device (1).

18. The hearing device (1) of claim 13, further comprising a classification unit (11) adapted to determine an acoustic situation, wherein the control unit (10) is further adapted to change the at least one setting or parameter of the filtering unit (3) dependent on the determined acoustic situation.

19. The hearing device (1) of claim 13, further comprising a counter (12) adapted to count the number of times the control signal has been initiated, wherein the control unit (10) is further adapted to change the at least one setting or parameter of the filtering unit (3) dependent on the number of times the control signal has been initiated, corresponding to the number of times the hearing device (1) has been activated or powered on.

20. The hearing device (1) of claim 13, wherein the control unit (10) is further adapted to incrementally change the at least one setting or parameter of the filtering unit (3) over time from a start value to an end value.

21. The hearing device (1) of claim 13, wherein a speed at which and/or an increment/decrement by which the at least one setting or parameter of the filtering unit (3) is changed is adjustable.

22. The hearing device (1) of claim 13, further comprising a timer (13), wherein the change of the at least one setting or parameter of the filtering unit (3) is dependent on a timer signal from the timer (13).

23. A hearing device (1) adapted for being worn at least partially within an ear canal of a user, the hearing device (1) comprising:
   an ear canal microphone (2);
   a filtering unit (3);
   an electrical-to-acoustical converter (4);
   an own voice detection unit (14) for detecting whether a body sound of the user is present or not and
   a control unit (10),
   wherein an output of the ear canal microphone (2) is connected to an input of the filtering unit (3), an output of the filtering unit (3) is operationally connected to an input of the electrical-to-acoustical converter (4), and an output of the control unit (10) is connected to a control input of the filtering unit (3), and wherein the control unit (10) is operationally connected or connectable to a control element (5, 5'), and the control unit (10) is adapted to receive a control signal initiated by the user and upon receiving the control signal to cause a change of at least one setting or parameter of the filtering unit (3), and wherein the control unit (10) is further adapted to only carry out the change of the at least one setting or parameter of the filtering unit (3) if a body sound of the user is detected as being present upon the control signal being initiated by the user or if a body sound of the user is detected as being present within less than 10 s after the control signal has been initiated.

24. The hearing device (1) of claim 13, further comprising a storage unit (9) for storing the changed at least one setting or parameter of the filtering unit (3).

\* \* \* \* \*